United States Patent [19]

Morningstar

[11] Patent Number: 5,512,054
[45] Date of Patent: Apr. 30, 1996

[54] DUAL ACTION SYRINGE

[75] Inventor: Randy L. Morningstar, Brooklyn Park, Minn.

[73] Assignee: American Medical Systems, Inc., Minnetonka, Minn.

[21] Appl. No.: 442,070

[22] Filed: May 16, 1995

[51] Int. Cl.[6] .................................................. A61M 5/00
[52] U.S. Cl. ............................................ 604/191; 604/218
[58] Field of Search ..................................... 604/191, 218, 604/187, 207, 208

[56] References Cited

U.S. PATENT DOCUMENTS

| | | |
|---|---|---|
| 3,985,122 | 10/1976 | Topham ........................... 604/218 X |
| 4,188,949 | 2/1980 | Antoshkiw ........................... 604/218 |
| 4,583,974 | 3/1985 | Kokernak . | 
| 4,758,223 | 7/1988 | Rydell ........................... 604/191 X |
| 5,047,015 | 9/1991 | Foote et al. . | 
| 5,057,078 | 10/1991 | Foote et al. . |
| 5,209,732 | 5/1993 | Lampropoulos et al. . |
| 5,354,285 | 10/1994 | Mazurik et al. ........................... 604/191 |

Primary Examiner—John D. Yasko
Attorney, Agent, or Firm—Peter C. Richardson; Lawrence C. Akers; Mark Dryer

[57] ABSTRACT

A dual action syringe which comprises a hollow body defining a rear chamber and a front chamber, wherein the rear chamber has a greater internal cross-sectional area than the front chamber, a double action plunger mechanism comprising a primary plunger with a cross-section which matches the internal cross-section of the rear chamber and a secondary plunger telescopically mounted within the primary plunger and having a cross-section which matches the internal cross-section of the front chamber, the proximal end of the secondary plunger extending beyond the proximal end of the primary plunger and terminating in a handle which enables the plunger mechanism to be slidably moved relative to the hollow body.

6 Claims, 3 Drawing Sheets

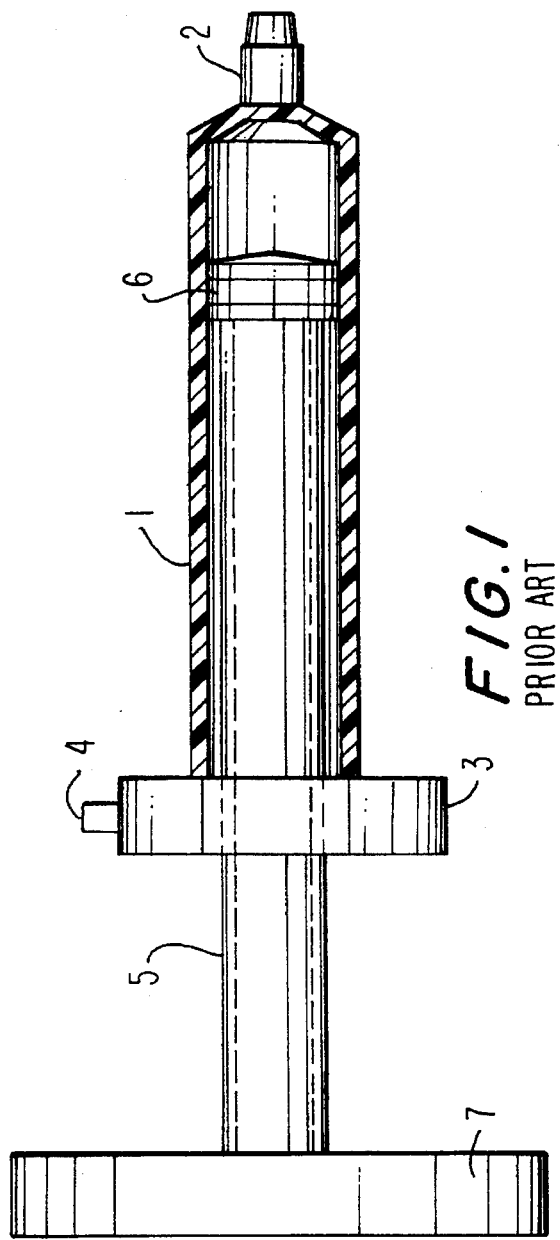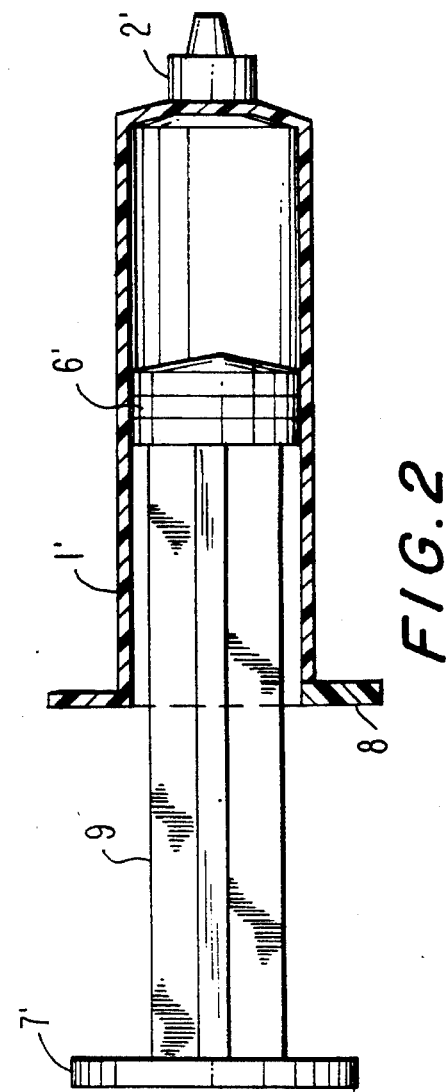

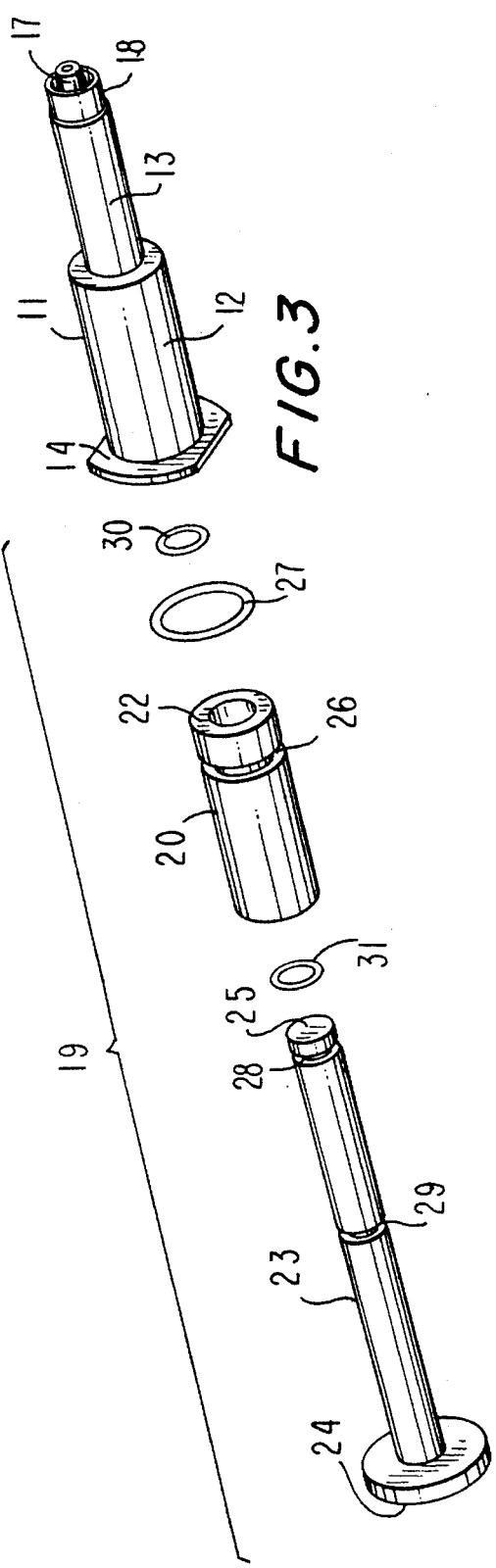
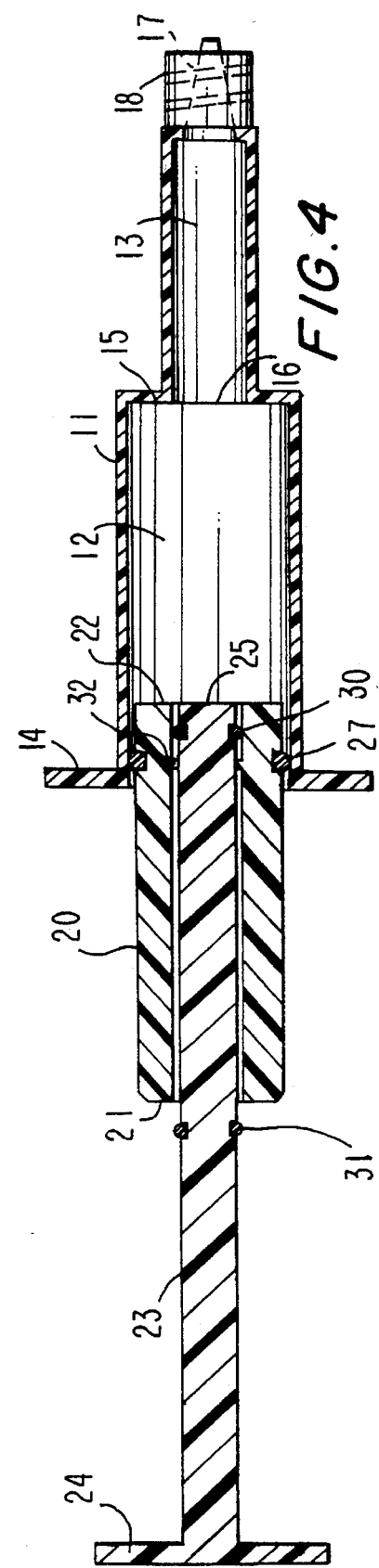

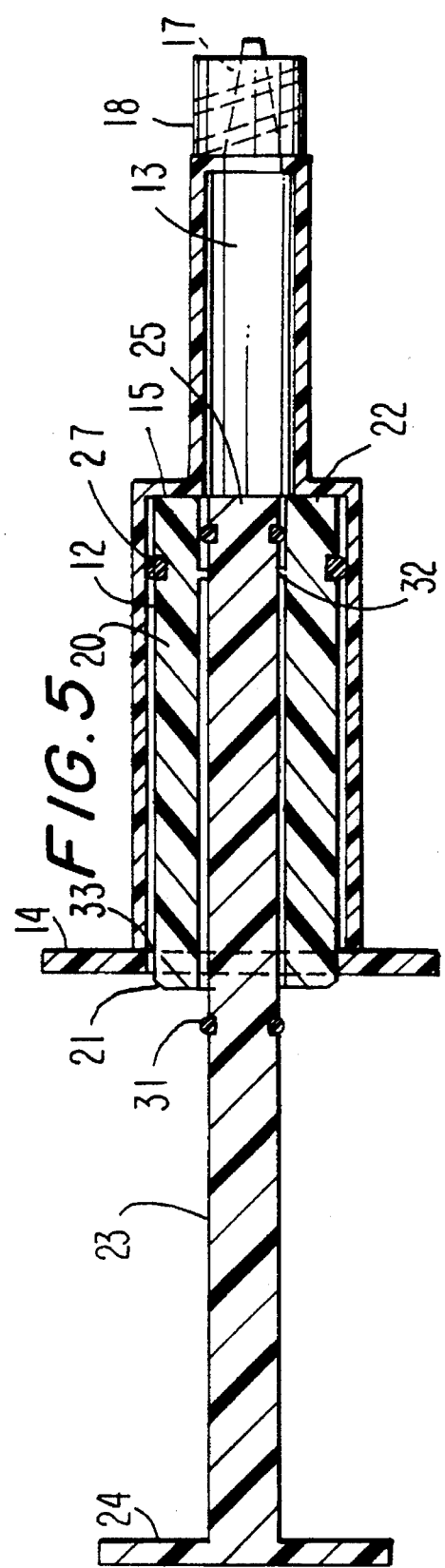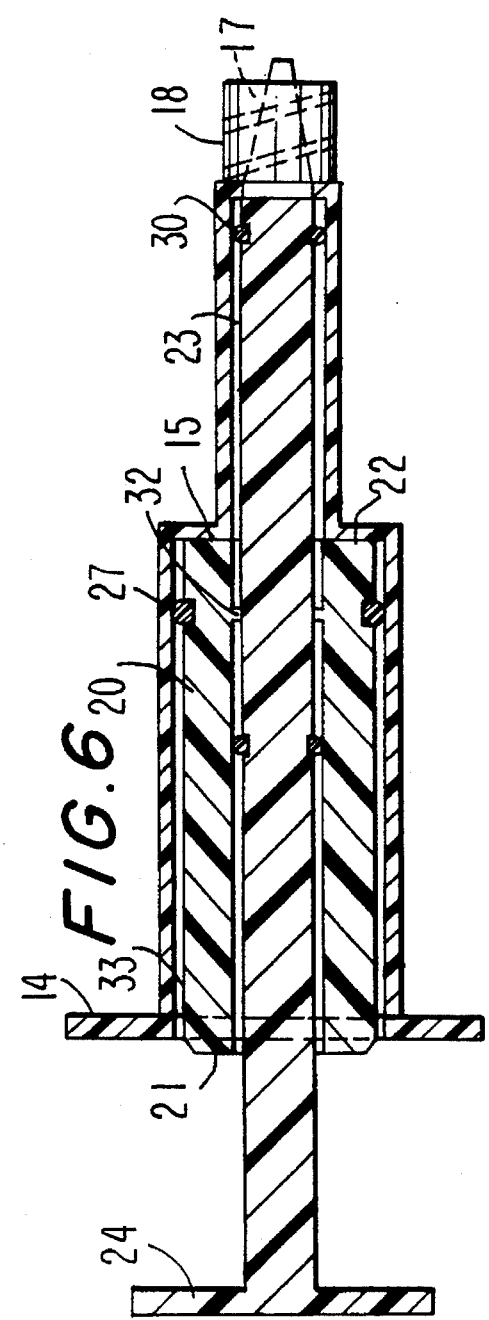

DUAL ACTION SYRINGE

FIELD OF THE INVENTION

This invention relates to a dual action syringe for delivering controlled volumes of fluid to a desired site. The syringe is particularly suitable for delivering liquid to inflate a medical device such as a balloon catheter.

BACKGROUND OF THE INVENTION

Syringes are known in the medical art for dispensing measured volumes of fluids, i.e., liquids or gases, to a given site. The typical syringe comprises a piston or plunger enveloped in a chamber, usually a cylindrical chamber, where it forms a fluid-tight seal with the wall of the chamber so that slidable movement of the plunger forwardly empties the chamber and backwardly refills the chamber.

Since the forward movement of the plunger exerts pressure on the fluid in the chamber, the fluid is delivered from the syringe under pressure and thus a syringe is a suitable instrument for inflating various inflatable devices such as balloon catheters. Balloon catheters have been used in various medical applications, for example, angioplasty and dilation of body lumens such as the prostatic urethra. For such applications an appreciable pressure is required to fully inflate the balloon.

While a standard, single plunger syringe is normally adequate to fill the balloon, it has been found that the maximum intended pressure for optimum working of the balloon cannot be achieved by a simple one-handed operation of the syringe. Various proposals have been made in the prior art to overcome this problem. For example, it has been proposed to enhance the pressure of the liquid delivered by the syringe by using a screw thread associated with the plunger mechanism. A disadvantage of this approach is that it requires two hands to operate.

Surprisingly, it has now been found that the desired maximum pressure can be achieved with a syringe that can be operated with one hand and is relatively inexpensive to manufacture by providing a dual action or dual pressure syringe which comprises a rear chamber and a front chamber of different cross-section area and a plunger mechanism comprising a primary plunger enveloping a telescopically slidable secondary plunger. The plunger mechanism co-operates with the chambers such that the rear chamber provides high volume and low pressure and the front chamber provides low volume and high pressure. The high pressure produced by the front chamber provides the necessary boost to achieve the intended pressure in the catheter balloon.

SUMMARY OF THE INVENTION

In accordance with the present invention there is provided a dual action syringe which comprises a hollow body having a rear portion and an integrally connected front portion, said portions defining a rear chamber having a proximal end and a distal end and a front chamber having a proximal end and a distal end, respectively, wherein the rear chamber has a greater internal cross-sectional area than the front chamber, a double action plunger mechanism comprising a primary plunger having a proximal end, a distal end and a cross-section which matches the internal cross-section of the rear chamber and a secondary plunger telescopically mounted within the primary plunger and having a proximal end, a distal end and a cross-section which matches the internal cross-section of the front chamber, the proximal end of the secondary plunger extending beyond the proximal end of the primary plunger and terminating in a handle which enables the plunger mechanism to be slidably moved relative to the hollow body (1) forwardly from a fully retracted position wherein the distal end of the secondary plunger is flush with the distal end of the primary plunger and the two plunger distal ends are adjacent the proximal end of the rear chamber, through a first discharge position where the two plunger distal ends are level with the distal end of the rear chamber, to a fully extended second discharge position where the secondary plunger is slidably extended forward from the distal end of the primary plunger until the distal end of the secondary plunger is level with the distal end of the front chamber, and (2) backwardly from said fully extended position to said fully retracted position.

Preferably the cross-section of each of the chambers and each of the plungers is circular.

In a preferred embodiment of the syringe according to the invention the primary plunger has a circumferential groove adjacent its distal end and the secondary plunger has a first circumferential groove adjacent its distal end and a second circumferential groove located proximal to the first groove, the distance between the first and second grooves being approximately equal to the length of the primary plunger, each of said grooves accommodating an O-ring seal, which seals prevent leakage of fluid behind the plunger mechanism and also control the frictional, sliding movement of each of the plungers.

Preferably the distal end of the front chamber terminates in a nozzle adapted to deliver fluid from the syringe to a desired site. It is also desirable that the nozzle be attached to or associated with a connector, for example, the female part of a luer connector, which enables the syringe to be connected to a device, for example, a balloon catheter, for leakage-free delivery of fluid.

To enable a suitable pressure differential to be achieved by the syringe for inflation of a balloon catheter it is preferred that the ratio between the cross-sectional area of the rear chamber and the cross-sectional area of the front chamber is from about 2:1 to 6:1; a suitable ratio being about 3:1.

In a preferred embodiment the body and plunger mechanism of the syringe are made from a clear transparent, substantially rigid plastic material, such as polyethylene (polythene). Usually these features are injection-molded. A preferred material for the O-ring seals is biocompatible, synthetic rubber. A particular advantage of these materials is ease of manufacture and low cost.

For many applications it is desirable to monitor the volume of fluid delivered by the syringe and to facilitate this it is preferred that the wall of the body of the syringe is calibrated with appropriate graduations, usually cc.

BRIEF DESCRIPTION OF THE DRAWINGS

For comparative purposes, examples of two prior art syringes are illustrated in the accompanying drawings in which:

FIG. 1 is a schematic representation of a prior art threaded syringe; and

FIG. 2 is a schematic representation of a prior art single action syringe.

A preferred embodiment of the invention is illustrated in the remaining figures of the drawings, in which:

FIG. 3 is an exploded perspective view of the syringe;

FIG. 4 is a side elevation, partly in section, showing the plunger mechanism in the fully retracted position;

FIG. 5 is a side elevation, partly in section, showing the first discharge position; and FIG. 6 is a side elevation, partly in section, showing the fully extended second discharge position.

DETAILED DESCRIPTION OF THE INVENTION

FIG. 1 of the drawings illustrates a prior art syringe having a threaded design. The syringe comprises a body 1 which is a hollow tube having a circular cross-section. The distal end of the body terminates in a nozzle 2. A threaded half nut 3 is integral with the proximal end of the body and this half nut is provided with a releasable lock 4. A plunger comprising a threaded shaft 5 is positioned to be slidably moved within the hollow body. The distal end of the plunger shaft accommodates a seal 6 which frictionally engages the wall of the syringe body. The proximal end of the shaft terminates in a handle 7 which enables the plunger to be slidably moved forwardly and backwardly within the hollow tubular body. When the lock 4 is released the plunger may be moved freely forward and backward within the hollow body. When the half nut is locked the plunger may be moved only by rotating the threaded shaft relative thereto. The screw thread enables maximum pressure to be exerted on the fluid delivered by the syringe but operation of this device usually requires two hands.

A standard prior art single action syringe is illustrated in FIG. 2 of the drawings. This syringe also comprises a hollow tube body 1' having a circular cross-section. The distal end of the body terminates in a nozzle 2'. The proximal end of the body terminates in a circular flange. A plunger comprising a fluted rigid shaft 9 is positioned to be slidably moved within the hollow body. The distal end of the plunger accommodates a seal 6' which frictionally engages the wall of the body. The proximal end of the shaft terminates in a handle 7'. Operation of the handle slidably moves the plunger with respect to the body. This syringe normally may be operated with one hand but the ultimate pressure obtained thereby is not always sufficient to fully inflate a balloon catheter to its optimum dilation.

A preferred embodiment of a syringe according to the invention is illustrated in FIGS. 3–6 of the drawings. The syringe comprises a hollow body 11 having a rear portion 12 and an integrally connected front portion 13. The rear portion defines a rear chamber having a proximal end which terminates in an external flange 14, and a distal end 15. The front portion defines a front chamber having a proximal end 16 which is integral with the distal end of the rear chamber and a distal end which terminates in a nozzle 17. The cross-section of both the rear chamber and the front chamber is circular and the internal cross-sectional area of the rear chamber is greater than that of the front chamber. In the illustrated embodiment, although not drawn to scale, the ratio between the cross-sectional area of the rear chamber and the cross-sectional area of the front chamber is about 3:1, providing an operational pressure differential of this order.

A standard luer type screw connector 18 is attached to the distal end of the front chamber to facilitate connection with a mating connector on the tube or device, for example, a balloon catheter, to be serviced by the syringe.

A double action plunger mechanism 19 adapted to be slidably moved within the hollow body comprises a primary plunger 20 having a proximal end 21 and a distal end 22, and a secondary plunger 23 having a proximal end which terminates in a handle 24, and a distal end 25. The primary plunger has a circumferential groove 26 which accommodates an O-ring seal 27 which provides a fluid-tight seal between the primary plunger and the internal wall of the rear chamber while still allowing slidable movement of the plunger within the chamber. The primary plunger has a coaxial tunnel extending longitudinally along its complete length, which tunnel is adapted to telescopically accommodate the secondary plunger 23.

The secondary plunger has a first circumferential groove 28 adjacent its distal end 25 and a second circumferential groove 29 located proximal to the first groove. The first groove accommodates an O-ring seal 30 and the second groove accommodates a similar O-ring seal 31.

In operating the syringe the secondary plunger is telescopically mounted within the coaxial tunnel of the primary plunger and the O-ring seals provide a fluid-tight seal between the secondary plunger and the inner wall of the tunnel as illustrated in FIGS. 4, 5 and 6 and between the secondary plunger and the internal wall of the front chamber as illustrated in FIG. 6.

The seals around the secondary plunger also serve to control the slidable movement of the combination primary and secondary plungers both relative to the rear and front chambers and to each other. A circumferential flange 32 on the inner wall of the tunnel adjacent the distal end of the primary plunger acts as a stop and prevents the secondary plunger from being pulled clear of the syringe. Likewise an internal lip 33 at the proximal end of the rear chamber prevents the primary plunger from being pulled clear of the syringe.

The syringe as described above is filled with liquid for inflating a balloon catheter by dipping the nozzle into a container of liquid, for example, sterile saline solution, with the plunger mechanism in the fully extended position (FIG. 6), and withdrawing the plunger mechanism to the fully retracted position (FIG. 4).

The filling of a high pressure balloon catheter by the syringe, filled with liquid as described above, is accomplished by attaching the catheter, through an appropriate connector, to the luer connector 18 and forcing the secondary plunger forward. The primary plunger is moved forward by the frictional contact with the second (rear) seal of the secondary plunger as the secondary plunger is pushed forward by the handle 24. Thus the plunger mechanism is moved forward as one unit from the fully retracted position of FIG. 4 to the first discharge position of FIG. 5, thus delivering the liquid in the rear chamber to the catheter. This delivery serves to initially fill the balloon of the catheter. When the frictional resistance of the rear seal is overcome by the force exerted on the secondary plunger, and coincidentally the distal end of the primary plunger reaches the distal end of the rear chamber, the primary plunger stops and the secondary plunger moves forward and into the front chamber whereby the rest of the liquid, present in the front chamber, is delivered to the catheter and this additional liquid volume provides the pressure required to bring the balloon to its intended pressure.

Calibrated gradations (usually in cc) on the wall of the syringe chambers (not shown) indicate the actual volume of liquid delivered.

To empty the balloon, the syringe operates in a similar way to that of any standard syringe. Thus withdrawal of the secondary plunger will in turn act on the primary plunger, thereby pulling back the entire plunger mechanism and extracting the liquid from the balloon.

I claim:

1. A dual action syringe which comprises a hollow body having a rear portion and an integrally connected front portion, said portions defining a rear chamber having a circular cross-section, a proximal end and a distal end and a front chamber having a circular cross-section, a proximal end and a distal end, respectively, wherein the rear chamber has a greater internal cross-sectional area than the front chamber, a double action plunger mechanism comprising a primary plunger having a proximal end, a distal end, a circumferential fluid-tight seal adjacent the distal end and a circular cross-section which matches the internal cross-section of the rear chamber and a secondary plunger telescopically mounted within the primary plunger and having a proximal end, a distal end, a first circumferential fluid-tight seal adjacent the distal end, a second circumferential fluid-tight seal located proximal to the first seal, the distance between the first and second seals being approximately equal to the length of the primary plunger and a circular cross-section which matches the internal cross-section of the front chamber, the proximal end of the secondary plunger extending beyond the proximal end of the primary plunger and terminating in a handle which enables the plunger mechanism to be slidably moved relative to the hollow body, (1) forwardly from a fully retracted position wherein the distal end of the secondary plunger is flush with the distal end of the primary plunger and the two plunger distal ends are adjacent the proximal end of the rear chamber, through a first discharge position where the two plunger distal ends are level with the distal end of the rear chamber, to a fully extended second discharge position where the secondary plunger is slidably extended forward from the distal end of the primary plunger until the distal end of the secondary plunger is level with the distal end of the front chamber, and (2) backwardly from said fully extended position to said fully retracted position.

2. A syringe according to claim 1, in which the primary plunger has a circumferential groove adjacent its distal end and the secondary plunger has a first circumferential groove adjacent its distal end and a second circumferential groove located proximal to the first groove, the distance between the first and second grooves being approximately equal to the length of the primary plunger, each of said grooves accommodating an O-ring seal, wherein the combination of grooves and O-ring seals provides said fluid-tight seals which prevent leakage of fluid behind the plunger mechanism and also control the frictional, sliding movement of each of the plungers.

3. A syringe according to claim 1, in which the distal end of the front chamber terminates in a nozzle adapted to deliver fluid from the syringe to a desired site.

4. A syringe according to claim 1, in which the ratio between the cross-sectional area of the rear chamber and the cross-sectional area of the front chamber is from about 2:1 to 6:1.

5. A syringe according to claim 2, in which the body and the plunger mechanism are made from clear transparent, substantially rigid, injection-molded polythene and each of the O-ring seals is made from biocompatible, synthetic rubber.

6. A syringe according to claim 5, in which the body has a wall calibrated with gradations to enable the user to monitor the volume of fluid delivered by the syringe.

* * * * *